(12) United States Patent
Zhou et al.

(10) Patent No.: US 9,867,878 B2
(45) Date of Patent: Jan. 16, 2018

(54) METHOD AND DEVICE FOR PRODUCING CRUDE COPPER

(71) Applicant: YANGGU XIANGGUANG COPPER CO., LTD., Shifo Town, Shandong (CN)

(72) Inventors: Songlin Zhou, Shandong (CN); Weidong Liu, Shandong (CN); Hu Wang, Shandong (CN)

(73) Assignee: Yanggu Xiangguang Copper Co., Ltd., Shifo Town, Shandong (CN)

( * ) Notice: Subject to any disclaimer, the term of this patent is extended or adjusted under 35 U.S.C. 154(b) by 160 days.

(21) Appl. No.: 14/650,245

(22) PCT Filed: May 21, 2014

(86) PCT No.: PCT/CN2014/077948
§ 371 (c)(1),
(2) Date: Jun. 5, 2015

(87) PCT Pub. No.: WO2015/010499
PCT Pub. Date: Jan. 29, 2015

(65) Prior Publication Data
US 2015/0322546 A1    Nov. 12, 2015

(30) Foreign Application Priority Data
Jul. 23, 2013  (CN) .......................... 2013 1 0314853

(51) Int. Cl.
*C22B 7/04* (2006.01)
*C22B 15/00* (2006.01)
(Continued)

(52) U.S. Cl.
CPC ........ *A61K 39/39558* (2013.01); *A61K 45/06* (2013.01); *A61K 47/6849* (2017.08);
(Continued)

(58) Field of Classification Search
CPC .... C22B 15/0024; C22B 7/04; C22B 15/0028
See application file for complete search history.

(56) References Cited

U.S. PATENT DOCUMENTS 3,281,236 A   10/1966  Meissner
3,857,701 A   12/1974  Hunter et al.
(Continued)

FOREIGN PATENT DOCUMENTS

CA   1225527        8/1987
CN   101705360   *  5/2010
(Continued)

OTHER PUBLICATIONS

JP 5357536 B2 published Dec. 2013. Machine translation.*
(Continued)

*Primary Examiner* — George Wyszomierski
*Assistant Examiner* — Tima M McGuthry Banks
(74) *Attorney, Agent, or Firm* — Schwabe Williamson & Wyatt, PC

(57) ABSTRACT

A method and device for producing a crude copper. The method comprises: mixing and reacting copper smelting molten slag (1), a carbon-containing reductant (2) and an inert gas (3) under pressure, the pressure of the inert gas (3) being 100 kPa to 800 kPa. The device comprises: a furnace body (4) and gas nozzles (411) disposed on the furnace body (4), the gas nozzles (411) being located on the sidewall of the furnace body (4) and connected to the center of the molten pool.

7 Claims, 1 Drawing Sheet

(51) Int. Cl.
  *A61K 39/395* (2006.01)
  *A61K 49/04* (2006.01)
  *A61K 49/16* (2006.01)
  *A61K 51/10* (2006.01)
  *C07K 16/18* (2006.01)
  *C07K 16/28* (2006.01)
  *A61K 45/06* (2006.01)
  *A61K 47/68* (2017.01)
  *A61K 38/00* (2006.01)
  *A61K 39/00* (2006.01)

(52) U.S. Cl.
  CPC .............. *A61K 49/04* (2013.01); *A61K 49/16* (2013.01); *A61K 51/1027* (2013.01); *A61K 51/1093* (2013.01); *C07K 16/18* (2013.01); *C07K 16/28* (2013.01); *C07K 16/2836* (2013.01); *A61K 38/00* (2013.01); *A61K 2039/505* (2013.01); *C07K 2319/74* (2013.01)

(56) References Cited

U.S. PATENT DOCUMENTS

| | | |
|---|---|---|
| 4,168,156 A | 9/1979 | Shabalina et al. |
| 4,802,916 A | 2/1989 | Victorovich |
| 6,231,641 B1 | 5/2001 | Utigard et al. |
| 2010/0107820 A1 | 5/2010 | Euston |

FOREIGN PATENT DOCUMENTS

| | | |
|---|---|---|
| CN | 101705360 A | 5/2010 |
| CN | 101736112 A | 6/2010 |
| CN | 101839631 A | 9/2010 |
| CN | 103014369 A | 4/2013 |
| CN | 103334014 A | 10/2013 |
| CN | 103388082 A | 11/2013 |
| JP | S5310306 A | 1/1978 |
| JP | 5357536 B2 * | 12/2013 |
| RU | 2169202 C1 | 6/2001 |
| RU | 2359046 C1 | 6/2009 |

OTHER PUBLICATIONS

CN 101705360 A published May 2010. Machine translation.*
Songlin Zhou. CN 101705360 published May 2010. Machine translation.*
Official Action of Substantive Examination for RU 2015124058 / 02(037544); dated Apr. 3, 2017; 13 pages including English translation.

* cited by examiner

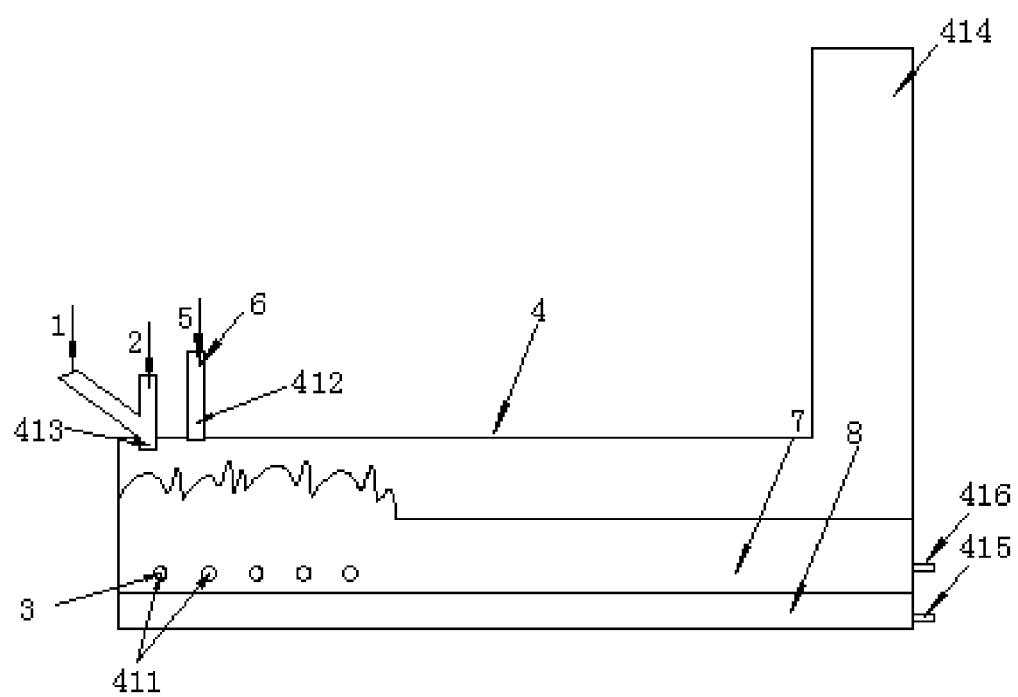

METHOD AND DEVICE FOR PRODUCING CRUDE COPPER

The present application is a U.S. National Phase of PCT/CN2014/077,948, filed May 21, 2014 entitled "Method and Device for Producing Crude Copper," which claims priority to the Chinese patent application No. 201310314853.8 filed with the Chinese Patent Office (SIPO) on Jul. 23, 2013 entitled "Method for production of blister copper and production device for use in production of blister copper", which are incorporated herein by reference in their entirety

FIELD OF THE INVENTION

The present invention relates to the technical field of nonferrous metallurgy, in particular, to a method for production of blister copper and a production device for use in production of blister copper.

BACKGROUND OF THE INVENTION

In copper pyrometallury industry, one method is producing blister copper indirectly from sulfide copper concentrate, which generally comprises two steps: first the sulfide copper concentrate is subjected to desulfurization and iron removal and smelting to obtain high-grade copper matte; and then the resulting copper matte is further subjected to desulfurization and iron removal and converting to give blister copper. Another method is producing blister copper directly from copper concentrate, which is adopted in practical production by Olympic Dam smeltery in Australia, Glogow smeltery in Poland, and KCM smeltery in Zambia. The blister copper produced by these copper smelting methods generally has a copper content of 98.5% by weight. However, these methods have a common feature that the slag resulted from production contains $Cu_2O$ and $Fe_3O_4$ in a relatively large amount. In general, the slag contains 10% to 20% by weight of copper, and 30% to 50% by weight of $Fe_3O_4$, which leads to waste of a large amount of resources.

SUMMARY OF THE INVENTION

In order to solve the above technical problem, the present invention provides a method for production of blister copper and a production device for use in production of blister copper. By the method, blister copper can be produced and the resulting slag has a low copper content.

The present invention provides a method for production of blister copper, comprising the following steps:

in a production device, mixing copper-smelting molten slag, carbon-containing reducing agent and pressurized inert gas followed by reaction to obtain blister copper and post-reaction slag, wherein the pressure of the inert gas is 100 kPa to 800 kPa.

Preferably, the production device comprises:

a furnace body, which furnace body comprises a molten pool inside and is provided therein with a gas nozzle, a feed port, a blister copper discharge port and a slag discharge port;

wherein the gas nozzle is disposed on the sidewall of the furnace body and leads to the middle part of the molten pool.

Preferably, the copper-smelting molten slag and the carbon-containing reducing agent are introduced to the production device via the feed port through a runner, respectively;

The inert gas is charged to the production device via the gas nozzle.

Preferably, the furnace body is provided with a fuel burner on the top;

Fuel and a combustion improver are directed to the fuel burner.

Preferably, the combustion improver is industrial oxygen gas with an oxygen concentration of greater than 95% by weight.

Preferably, the inert gas is nitrogen gas.

Preferably, the copper-smelting molten slag is at a temperature of 1050° C. to 1350° C.

Preferably, the carbon-containing reducing agent is at least one of coke and coal.

Preferably, a ratio by mass of carbon content in the carbon-containing reducing agent to oxygen content in the copper-smelting molten slag is (0.1-0.35):1.

The present invention further provides a production device for use in production of blister copper, comprising:

a furnace body, which furnace body comprises a molten pool inside and is provided therein with a gas nozzle, a feed port, a blister copper discharge port and a slag discharge port;

wherein the gas nozzle is disposed on the sidewall of the furnace body and leads to the middle part of the molten pool.

In comparison with the prior art, the present invention introduces copper-smelting molten slag and a carbon-containing reducing agent to a production device, charges pressurized inert gas with a pressure of 100 kPa to 800 kPa to the production device, mixes the materials and performs reaction to obtain blister copper and post-reaction slag. In the present invention, sensible heat of the copper-smelting molten slag is utilized to enable the carbon-containing reducing agent to reach red-hot state, and $Cu_2O$ in the slag is reduced to metal copper by the red-hot carbon-containing reducing agent, at the same time $Fe_3O_4$ in the slag is reduced to FeO. The charged inert gas agitates the reaction materials intensively, makes the molten slag boil, draws the carbon-containing reducing agent into the molten slag, and promotes the generated small droplets of molten copper to combine with each other so as to form separated blister copper phase and slag phase. By intensive agitating with inert gas, the present invention promotes rapidly refreshing of the reaction interface, intensifies the reaction progress, changes property of the slag rapidly, reduces viscosity of the slag, and increases probability of collision and combination among molten copper droplets thereby to facilitate sedimentation of molten copper droplets. Consequently, blister copper can be obtained in the intensified process of the present invention and the copper content in the final slag can be reduced. It is shown in practice that by the present invention, blister copper with a copper content greater than 98.5% by weight can be produced and copper content in the final slag is reduced to 0.4% by weight or less.

BRIEF DESCRIPTION OF THE DRAWINGS

FIG. 1 is a structural schematic diagram of the production device used in blister copper production that is provided in the examples of the present invention.

DETAILED DESCRIPTION OF THE INVENTION

For further understanding of the present invention, preferred embodiments of the present invention are depicted below in combination with examples, but it should be understood that these depiction are merely to further illustrate features and merits of the present invention, rather than to limit the claims of the present invention.

The present invention provides a method for production of blister copper, comprising the following steps:

in a production device, mixing copper-smelting molten slag, carbon-containing reducing agent and pressurized inert gas followed by reaction to obtain blister copper and post-reaction slag, wherein the pressure of the inert gas is 100 kPa to 800 kPa.

To adapt to development of metallurgy and overcome deficiency of the prior art, the production method for blister copper provided by the present invention is a method of producing blister copper directly from molten slag rich in $Cu_2O$ and $Fe_3O_4$ which is resulted from copper smelting. By the method, not only blister copper can be obtained, but also copper content in the treated slag can be decreased, such that the final slag, without further treatments like beneficiation, can serve as a raw material for other industries after being granulated, and thus allow low investment and production cost. Therefore, the method of the present invention can be considered as a method of cleaning copper-smelting molten slag.

In an example of the present invention, copper-smelting molten slag and a carbon-containing reducing agent are introduced in a production device, and pressurized inert gas at a pressure of 100 kPa to 800 kPa is charged to the production device. Then, the materials are mixed to perform reaction, thereby to obtain blister copper and post-reaction slag.

The present invention produces blister copper by using copper-smelting molten slag as a raw material, and has high economic benefit and social benefit. The copper-smelting molten slag is a slag rich in $Cu_2O$ and $Fe_3O_4$ in molten state that is resulted from copper smelting well known to those skilled in the art. In the present invention, there is no special limitation to components of the copper-smelting molten slag, where copper is in oxidized state and generally in an amount of 10% to 20% by weight, and $Fe_3O_4$ is generally in an amount of 30% to 50% by weight. The copper-smelting molten slag has sensible heat, and temperature thereof is preferably 1050° C. to 1350° C. The present invention utilizes sensible heat of the copper-smelting molten slag to make the carbon-containing reducing agent reach red-hot state, and there is not need to supplement additional heat to assist temperature rise of the carbon-containing reducing agent, thereby achieving good energy-saving effect and saving economic cost.

In the present invention, a carbon-containing reducing agent is mixed with the copper-smelting molten slag to reduce the $Cu_2O$ in the slag into metal copper and meanwhile to reduce $Fe_3O_4$, thereby to obtain blister copper and clean the slag. The carbon-containing reducing agent is granulated, and it is preferably at least one of coal and coke, more preferably coke. There is no special limitation to the source of the carbon-containing reducing agent in the present invention. In the present invention, a ratio by mass of carbon content in the carbon-containing reducing agent to oxygen content in the copper-smelting molten slag (C/O) is preferably (0.1-0.35):1.

In the present invention, the power for making molten slag boil and generating intensive agitating action is supplied by charging pressurized inert gas to the above reaction materials. Specifically, the charged inert gas intensively agitates the reaction materials, makes the molten slag boil, draws the carbon-containing reducing agent into the molten slag, and promotes the generated small droplets of molten copper to combine with each other so as to form separated blister copper phase and slag phase.

By intensive agitating with inert gas, the present invention promotes rapidly refreshing of the reaction interface, intensifies the reaction progress, changes property of the slag rapidly, reduces viscosity of the slag, and increases probability of collision and combination among molten copper droplets thereby to facilitate sedimentation of molten copper droplets. Consequently, blister copper can be obtained in the intensified process of the present invention, and copper content in the final slag can be reduced. In addition, agitating with inert gas can prevent the carbon-containing reducing agent and generated blister copper from being oxidized, and decrease usage amount of the carbon-containing reducing agent and allow high efficiency and low cost.

In the present invention, the inert gas has a pressure of 100 kPa to 800 kPa, preferably 200 kPa to 600 kPa, more preferably, 300 kPa to 500 kPa. The inert gas is preferably nitrogen gas, and it can increase contact among reaction materials and improve reaction efficiency. Moreover, nitrogen gas as an inert gas would not re-oxidize the reduced Cu and FeO, being beneficial to blister copper production.

It is preferred in the present invention to introduce copper-smelting molten slag to a production device, proportionally add a carbon-containing reducing agent and charge pressurized inert gas to the production device. In the present invention, the production device is preferably a production device described as follows.

The present invention provides a production device for use in production of blister copper, comprising:

a furnace body, which furnace body comprises a molten pool inside and is provided therein with a gas nozzle, a feed port, a blister copper discharge port and a slag discharge port;

The gas nozzle is disposed on the sidewall of the furnace body and leads to the middle part of the molten pool.

The production device provided by the present invention is used in production of blister copper, and facilitates to obtain blister copper and decrease the copper content of the treated slag.

The production device for use in production of blister copper provided in examples of the present invention is a side-blown metallurgical furnace, whose structure is shown in FIG. 1. FIG. 1 is a structural schematic diagram of the production device used in blister copper production that is provided in the examples of the present invention.

In FIG. 1, 1 represents copper-smelting molten slag, 2 represents a carbon-containing reducing agent, 3 represents pressurized inert gas, 4 represents furnace body, 411 represents a gas nozzle, 412 represents a fuel burner, 413 represents a feed port, 414 represents a rising flue, 415 is a blister copper discharge port, 416 represents a slag discharge port, 5 represents fuel, 6 represents combustion improver, 7 represents a layer of unreacted carbon-containing reducing agent, 8 represents a slag layer, and 9 represents a blister copper layer.

In the present invention, furnace body 4 comprises a molten pool inside where production of blister copper is conducted mainly. In an example of the present invention, furnace body 4 further comprises therein a rising flue 414 which is in communication with the molten pool. The furnace gas generated in production process is discharged through the rising flue 414, cooled, dedusted and then exhausted.

Furnace body 4 is provided thereon with a feed port 413 through which copper-smelting molten slag and carbon-containing reducing agent are added. Preferably, copper-smelting molten slag 1 and carbon-containing reducing agent 2 are introduced to the production device via the feed port 413 through a runner, respectively.

Furnace body 4 is provided thereon with a gas nozzle 411, which is located on the sidewall of the furnace body and leads to the middle part of the molten pool. The middle part of the molten pool refers to the position corresponding to the formed slag layer. The gas nozzle 411 may be located in one sidewall or two sidewalls of the furnace body 4. In the present invention, there may be one or more, preferably 5, gas nozzles in one sidewall.

In the present invention, inert gas 3 is preferably introduced to the production device via the gas nozzle 411. Since the gas nozzle 411 is disposed on the sidewall of the furnace body 4 and can be immersed in the melt in the molten pool, i.e. the inert gas can be introduced to the slag layer, the introduced inert gas 3 can better provide the power for making molten slag boil and forming intensive agitation, without re-agitating the product into the slag. Thus, the inert gas facilitates sedimentation and separation of the product, and improves efficiency.

In an example of the present invention, furnace body 4 is provided on the top with a fuel burner 412 to which fuel 5 and combustion improver 6 are introduced. It is preferred in the present invention to combust fuel 5 in the fuel burner 412 to generate heat. Additionally, when the $Cu_2O$ and $Fe_3O_4$ in slag are reacted with the carbon-containing reducing agent 2, a certain amount of CO will be generated (it is not shown in FIG. 1), and combustion of the generated CO in the presence of air and combustion improver 6 will generate heat as well. The air is inhaled via the feed port 413, and the generated heat can maintain thermal equilibrium of the reduction reaction. Fuels commonly used in the art are employed. The combustion improver is preferably industrial oxygen gas with an oxygen concentration of greater than 95% by weight to ensure a small amount of furnace gas, such that the heat carried away by furnace gas is small enough. There is no special limitation to amounts of the fuel and combustion improver in the present invention, as long as the total heat generated in combustion can maintain thermal equilibrium of the reduction reaction.

In the present invention, a blister copper discharge port 415 is arranged on the furnace body 4, and disposed at the lower part of the sidewall of the furnace body 4. The lower part of the sidewall refers to the position corresponding to the formed blister copper layer. Blister copper is discharged via the blister copper discharge port 415, and may be delivered to an anodic refining furnace to carry out blister copper refining.

In the present invention, a slag discharge port 416 is arranged on the furnace body for discharging slag. In an example of the present invention, feed port 413 is located on top at one end of the furnace body 4, and reaction materials may be added proportionally and continuously. The slag discharge port 416 is located at lower part of the other end of the furnace body 4. Newly-generated slag is discharged continuously from the slag discharge port 416 and may be granulated to serve as a raw material for other industries.

There is no special limitation to materials and sizes of the furnace body, gas nozzle, and fuel burner in the present invention, and materials and sizes commonly used in the art are employed. Sizes of the feed port, slag discharge port, blister copper discharge port, molten pool and rising flue are technical content well known to those skilled in the art, and there is no special limitation to them in the present invention.

When blister copper production is carried out according to an example of the present invention, copper-smelting molten slag 1 is introduced to the furnace body 4 via the feed port 413 through a runner at one end of the furnace body 4, carbon-containing reducing agent 2 is proportionally added via the feed port 413 through a runner, and pressurized inert gas 3 is continuously charged via the gas nozzles 411 which are disposed on two sidewalls of the furnace body 4 and immersed in the melt in the molten pool, to make the molten slag boil and to draw the granulated carbon-containing reducing agent in the molten slag so as to form a mixture.

In the process, sensible heat of the slag renders the carbon-containing reducing agent red-hot, and the red-hot carbon-containing reducing agent reduces copper compound $Cu_2O$ carried in the slag to metal copper. At the same time, iron compound carried in slag is converted from high-melting-point $Fe_3O_4$ to FeO. Further, FeO and $SiO_2$ carried in the slag make slag and form $2FeO.SiO_2$ with a lower melting point, so as to change properties of the slag and reduce viscosity thereof, which is beneficial to sedimentation and separation of copper and slag. The introduced inert gas agitates the reaction materials intensively, promotes rapidly refreshing of the reaction interface, intensifies the reaction progress, and changes property of the slag rapidly, and meanwhile promotes the generated small droplets of molten copper to combine with each other so as to form separated slag layer 8 and blister copper layer 9 in the furnace body 4.

The redundant and unreacted carbon-containing reducing agent floats on surface of the slag due to lower density thereof to form a layer of red-hot solid unreacted carbon-containing reducing agent 7. The layer of red-hot solid unreacted carbon-containing reducing agent 7 isolates the slag layer 8 and blister copper layer 9 in liquid phase from the above air layer, thereby preventing FeO in the slag layer and Cu in the blister copper layer from contacting with $O_2$ in air layer and making sure the reduced copper and slag would not be re-oxidized.

Also, according to an example of the present invention, fuel 5 and combustion improver 6 are introduced to the fuel burner 412 disposed on the top of the furnace body 4, and thermal equilibrium of the reduction reaction is maintained by combustion of the fuel 5 and CO in the burner. The combustion improver 6 used for combustion of the fuel 5 is industrial oxygen gas with an oxygen concentration of greater than 95% by weight, to ensure a small amount of furnace gas, so as to guarantee heat carried away by furnace gas is small enough.

At the other end of the furnace body 4, slag in liquid phase is discharged from the slag discharge port 416, and blister copper in liquid phase is discharged from the blister copper discharge port 415 that is disposed at lower part of the sidewall of the furnace body 4. Besides, the furnace gas generated in the above process is discharged via the rising flue 414, cooled, dedusted, desulfurized and then exhausted.

Separated blister copper and new slag are obtained after completion of the production. According to testing standard in the art, the slag contains copper in an amount of 0.4% by weight or less, and it can serve as a raw material for other industries after being granulated. The blister copper contains copper in an amount of greater than 98.5% by weight, and may be delivered to an anodic refining furnace to carry out blister copper refining.

In summary, the method for production of blister copper provided in the present invention has high reaction efficiency, and obtains blister copper from copper-smelting molten slag with low copper content in slag. In addition, the method of the present invention not only is simple in process and convenient for control and operation, but also has the merits of small device, low energy consumption, less investment and suitability for generalization.

For further understanding of the present invention, the method for production of blister copper and production device used in production of blister copper provided in the present invention are particularly described in combination with examples below.

The copper-smelting molten slag used in the following examples has a copper content of 20% and an oxygen content of 30%, and it is at a temperature of 1250° C.

EXAMPLE 1

In the production device shown in FIG. 1, copper-smelting molten slag 1 was introduced to the furnace body 4 via the feed port 413 through a runner, coke 2 was proportionally added via the feed port 413 through a runner, and pressurized nitrogen gas 3 was continuously introduced via the gas nozzles 411 that were disposed in two sidewalls of the furnace body 4 and immersed in the melt in the molten pool. The materials were mixed followed by reaction. Separated slag layer 8 and blister copper layer 9 were formed in the furnace body 4, and the redundant and unreacted coke formed an unreacted coke layer 7.

The raw slag was treated at a rate of 100 t/h, coke was added at a rate of 4.2 t/h; the nitrogen gas was at a pressure of 100 kPa; and a ratio by mass of carbon content in the coke to oxygen content in the copper-smelting molten slag (C/O) was (0.1-0.35):1.

Fuel 5 and industrial oxygen gas 6 were introduced to the fuel burner 412 disposed on the top of the furnace body 4, and thermal equilibrium of the reduction reaction was maintained by combustion of the fuel 5 and CO in the burner.

Slag in liquid phase was discharged via the slag discharge port 416, and blister copper in liquid phase was discharged from the blister copper discharge port 415 that was disposed at lower part of the sidewall of the furnace body 4. In addition, the furnace gas generated in the above process was discharged via the rising flue 414, cooled, dedusted, desulfurized and then exhausted.

After obtaining separated blister copper and new slag, according to testing standard in the art, the slag contains copper in an amount of 0.4% by weight, and the blister copper contains copper in an amount of 98.5% by weight.

EXAMPLE 2

Separated blister copper and new slag were obtained according to the method of example 1 with nitrogen gas at a pressure of 800 kPa and a ratio of by mass of carbon content in the coke to oxygen content in the copper-smelting molten slag (C/O) being (0.1-0.35):1.

According to testing standard in the art, the slag contains copper in an amount of 0.4% by weight, and the blister copper contains copper in an amount of 98.5% by weight.

From the above examples, it can be seen that the method for production of blister copper provided by the present invention can not only obtain blister copper, but also decrease copper content in the treated slag, such that the final slag, without further treatments such as beneficiation, can serve as a raw material for other industries after being granulated, therefore allowing low in cost for investment and production.

In addition, the method of the present invention has the merits of simple process and convenient control and operation, and is applicable to be generalized.

The above illustration with examples is merely to aid understanding of the method of the present invention and core idea thereof. It should be indicated that several improvements and modifications may be made by an ordinary artisan skilled in the art without deviation from the principle of the present invention, and such improvements and modifications all fall within the protection scope covered by the claims of the present invention.

What is claimed is:

1. A method for production of blister copper, comprising the following steps:
   in a production device, mixing copper-smelting molten slag, a carbon-containing reducing agent and pressurized inert gas followed by reaction to obtain blister copper and post-reaction slag, wherein the inert gas has a pressure of 100 kPa to 800 kPa, and wherein the production device comprises:
   a furnace body, which furnace body comprises a molten pool inside and is provided therein with a gas nozzle, a feed port, a blister copper discharge port and a slag discharge port;
   wherein the gas nozzle is disposed on the sidewall of the furnace body and leads to the middle part of the molten pool; and
   wherein the copper-smelting molten slag and the carbon-containing reducing agent are introduced to the production device via the feed port through a runner, respectively;
   the inert gas is charged to the production device via the gas nozzle.

2. The production method according to claim 1, wherein the furnace body is provided with a fuel burner on the top; fuel and a combustion improver are introduced to the fuel burner.

3. The production method according to claim 2, wherein the combustion improver is industrial oxygen gas with an oxygen concentration of greater than 95% by weight.

4. The production method according to claim 1, wherein the inert gas is nitrogen gas.

5. The production method according to claim 1, wherein the copper-smelting molten slag is at a temperature of 1050° C. to 1350° C.

6. The production method according to claim 1, wherein the carbon-containing reducing agent is at least one of coke and coal.

7. The production method according to claim 6, wherein a ratio by mass of carbon content in the carbon-containing reducing agent to oxygen content in the copper-smelting molten slag is (0.1-0.35):1.

* * * * *